United States Patent
McGregor et al.

(10) Patent No.: US 12,226,149 B2
(45) Date of Patent: *Feb. 18, 2025

(54) SYSTEM AND METHOD FOR ADJUSTING AVAILABLE POWER PER PROBE DURING AN ABLATION PROCEDURE

(71) Applicant: Avent, Inc., Alpharetta, GA (US)

(72) Inventors: Lisa M. McGregor, Chamblee, GA (US); Lee Rhein, Hollywood, FL (US); Tyler W. Crone, Atlanta, GA (US); Jennifer J. Barrett, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 966 days.

This patent is subject to a terminal disclaimer.

(21) Appl. No.: 17/234,414

(22) Filed: Apr. 19, 2021

(65) Prior Publication Data
US 2021/0236200 A1 Aug. 5, 2021

Related U.S. Application Data

(63) Continuation of application No. 16/027,653, filed on Jul. 5, 2018, now Pat. No. 10,980,599.

(51) Int. Cl.
*A61B 18/18* (2006.01)
*A61B 18/12* (2006.01)
(Continued)

(52) U.S. Cl.
CPC ...... *A61B 18/1492* (2013.01); *A61B 18/1206* (2013.01); *A61B 2018/00577* (2013.01);
(Continued)

(58) Field of Classification Search
CPC .............. A61B 18/1206; A61B 18/148; A61B 18/1492; A61B 2018/00023;
(Continued)

(56) References Cited

U.S. PATENT DOCUMENTS 5,542,916 A 8/1996 Hirsch et al.
5,718,701 A 2/1998 Shai et al.
(Continued)

FOREIGN PATENT DOCUMENTS

EP 2653128 10/2013
EP 2942023 11/2015
WO 2018116247 6/2018

OTHER PUBLICATIONS

International Search Report and Written Opinion issued for Application No. PCT/US2019/040229, dated Oct. 16, 2019, 18 pages.

*Primary Examiner* — Michael F Peffley
*Assistant Examiner* — Amanda L Zink
(74) *Attorney, Agent, or Firm* — Meunier Carlin & Curfman LLC

(57) ABSTRACT

An ablation system for treating tissue in a patient's body includes an energy source, one or more probes connected to the energy source, and a controller communicatively coupled to one or more probes. Each of the probes includes an elongate member having a distal region with an electrically non-conductive outer circumferential portion and a proximal region. The probes further include an electrically conductive energy delivery device extending distally from the electrically non-conductive outer circumferential portion. The controller includes one or more processors and one or more memory devices. The one or more memory devices are configured to store computer-readable instructions that when executed by the one or more processors cause the one or more processors to perform operations that include detecting a number of probes connected to the energy source and allocating a portion of the predetermined power supply to each of the probes.

19 Claims, 7 Drawing Sheets

(51) Int. Cl.
*A61B 18/14* (2006.01)
*A61B 18/00* (2006.01)

(52) U.S. Cl.
CPC .............. *A61B 2018/00702* (2013.01); *A61B 2018/00714* (2013.01); *A61B 2018/00797* (2013.01)

(58) Field of Classification Search
CPC .. A61B 2018/0044; A61B 2018/00577; A61B 2018/00654; A61B 2018/00702; A61B 2018/00714; A61B 2018/00797; A61B 2018/00875; A61B 2018/124
See application file for complete search history.

(56) References Cited

U.S. PATENT DOCUMENTS

| | | | |
|---|---|---|---|
| 5,957,961 A | 9/1999 | Maguire et al. | |
| 6,231,569 B1 | 5/2001 | Bek et al. | |
| 6,346,104 B2 | 2/2002 | Daly et al. | |
| 6,470,219 B1 | 10/2002 | Edwards et al. | |
| 7,125,407 B2 | 10/2006 | Edwards et al. | |
| 8,486,065 B2 | 4/2013 | Lee et al. | |
| 8,771,269 B2 | 7/2014 | Sherman et al. | |
| 8,998,893 B2 | 4/2015 | Avitall | |
| 9,044,245 B2 | 6/2015 | Condie et al. | |
| 9,168,093 B2 | 10/2015 | Mihalik et al. | |
| 9,375,154 B2 | 6/2016 | Wang | |
| 9,387,032 B2 | 7/2016 | Martin et al. | |
| 9,539,052 B2 | 1/2017 | Edwards et al. | |
| 9,561,070 B2 | 2/2017 | Brotz et al. | |
| 2008/0065062 A1 | 3/2008 | Leung et al. | |
| 2008/0097557 A1 | 4/2008 | Eggers et al. | |
| 2008/0183169 A1* | 7/2008 | Klimovitch | A61N 7/02 606/42 |
| 2008/0234574 A1* | 9/2008 | Hancock | A61B 18/18 600/430 |
| 2009/0138011 A1 | 5/2009 | Epstein | |
| 2010/0324548 A1 | 12/2010 | Godara et al. | |
| 2013/0165919 A1 | 6/2013 | Epstein | |
| 2013/0331835 A1 | 12/2013 | Leung et al. | |
| 2014/0243823 A1 | 8/2014 | Godara et al. | |
| 2014/0276755 A1 | 9/2014 | Cao et al. | |
| 2014/0330266 A1 | 11/2014 | Thompson et al. | |
| 2015/0133917 A1 | 5/2015 | Edwards et al. | |
| 2017/0049513 A1* | 2/2017 | Cosman, Jr. | A61B 18/18 |
| 2020/0085487 A1 | 3/2020 | Godara et al. | |

* cited by examiner

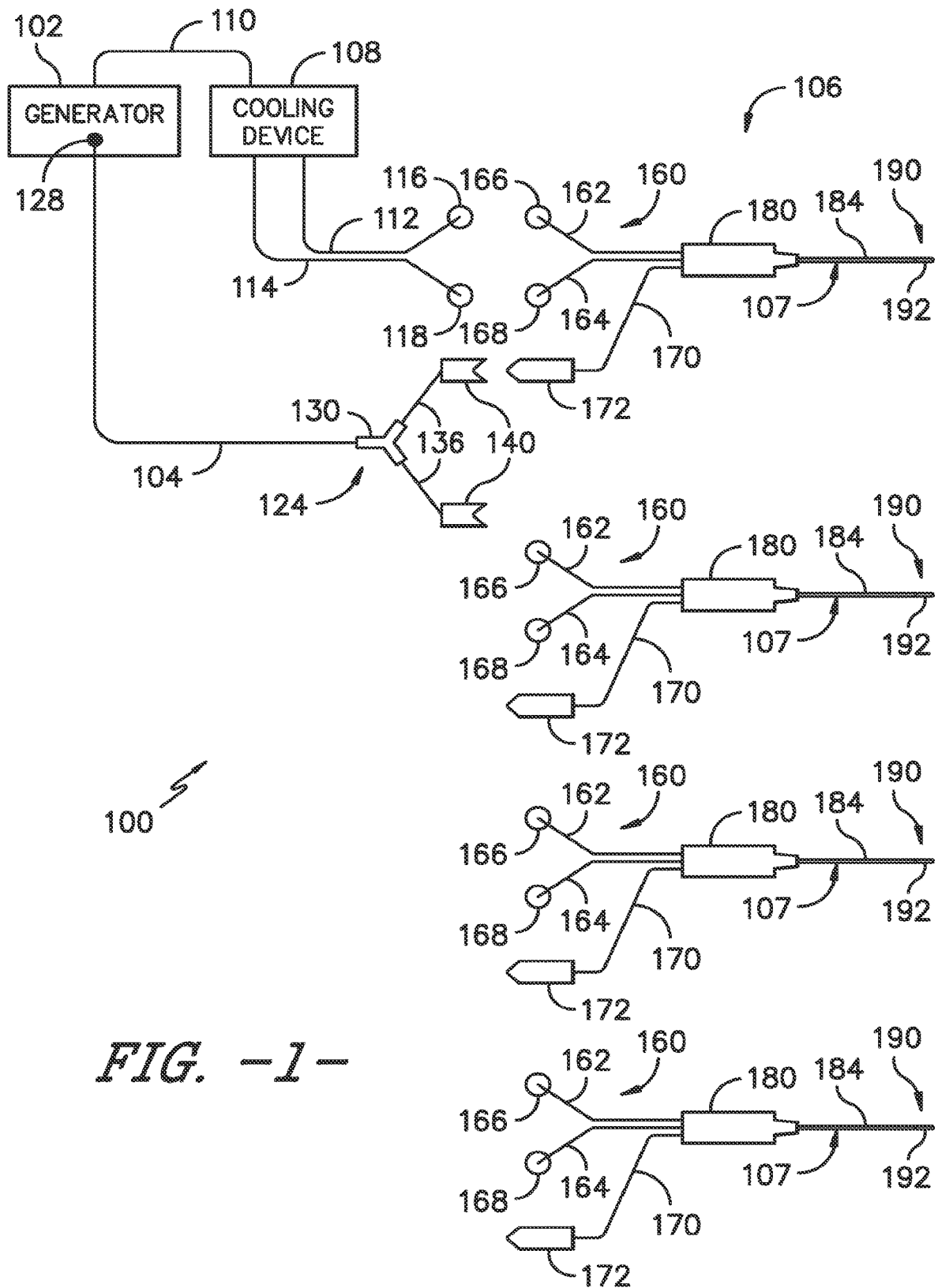
FIG. -1-

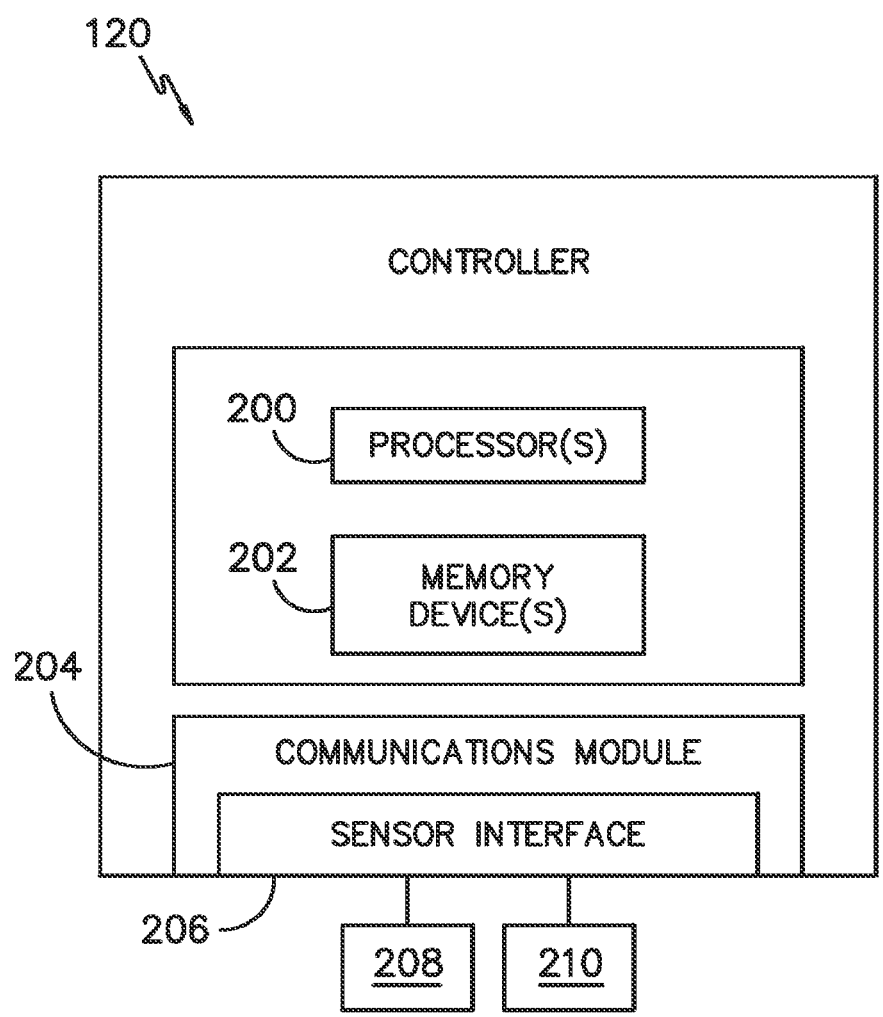
FIG. -2-

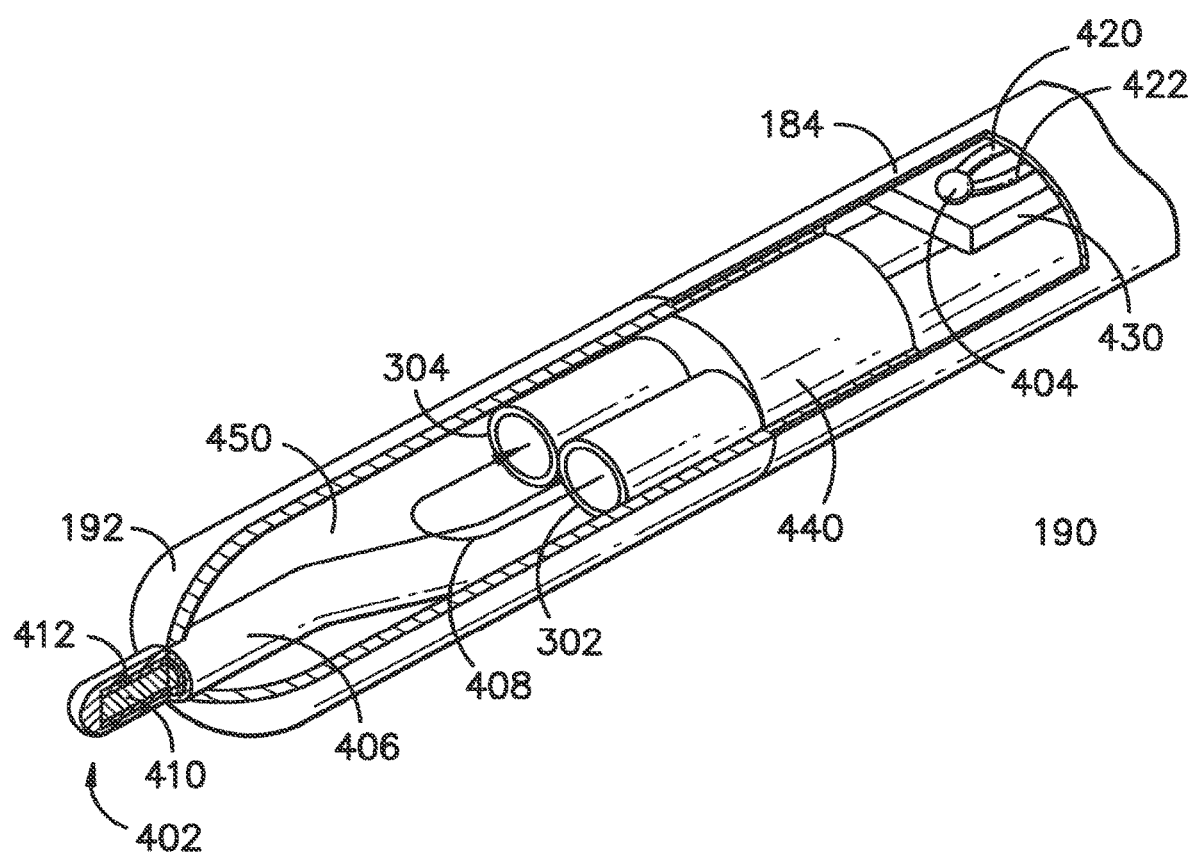
FIG. -3-

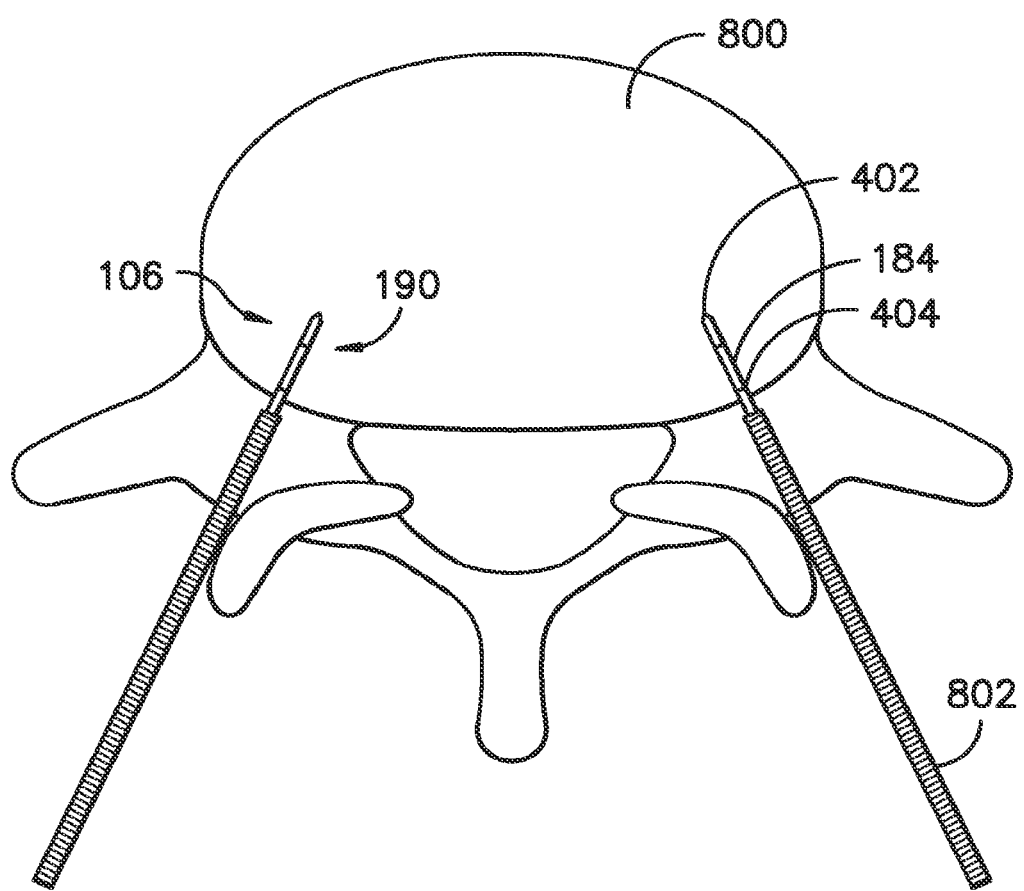
FIG. -4-

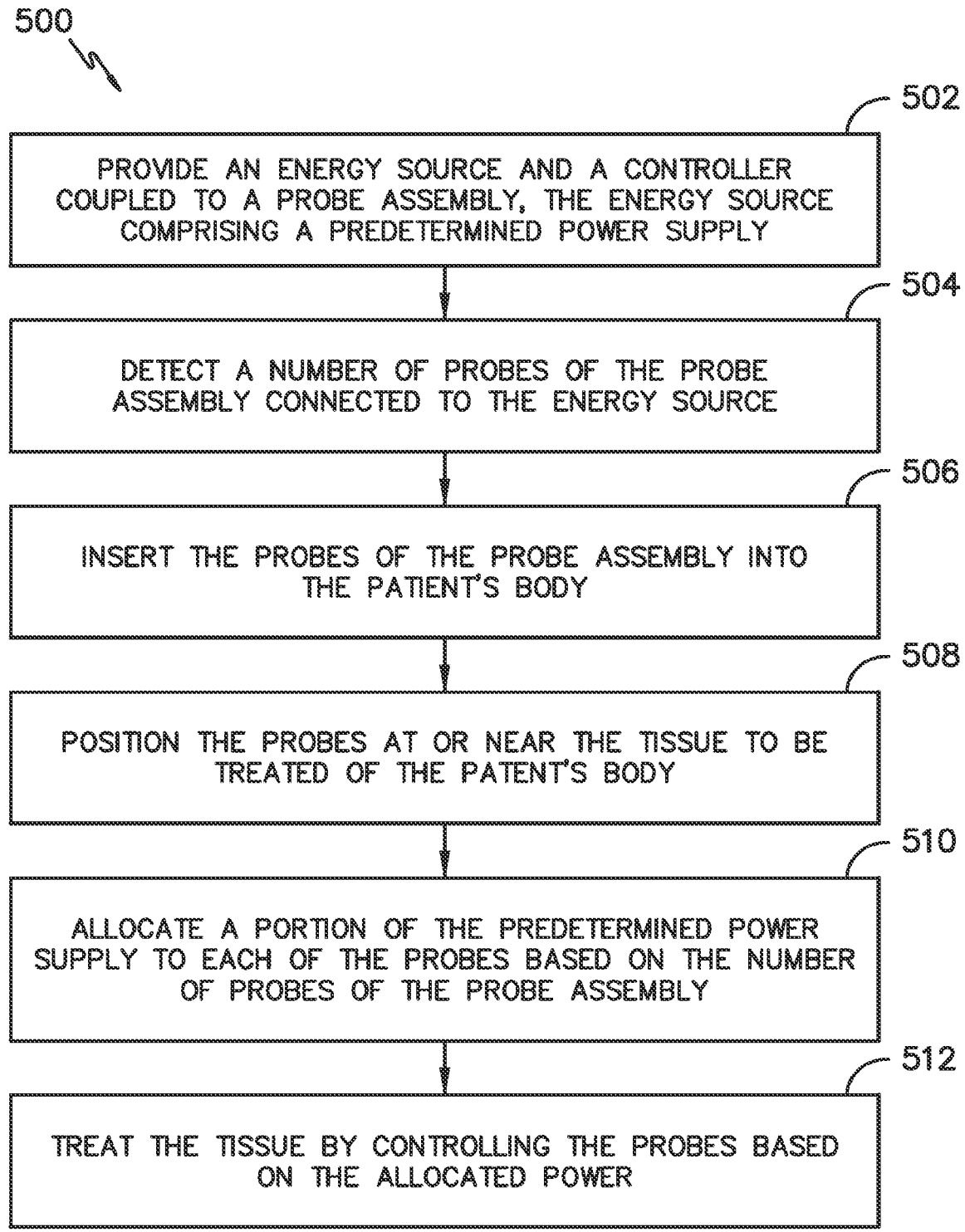
FIG. -5-

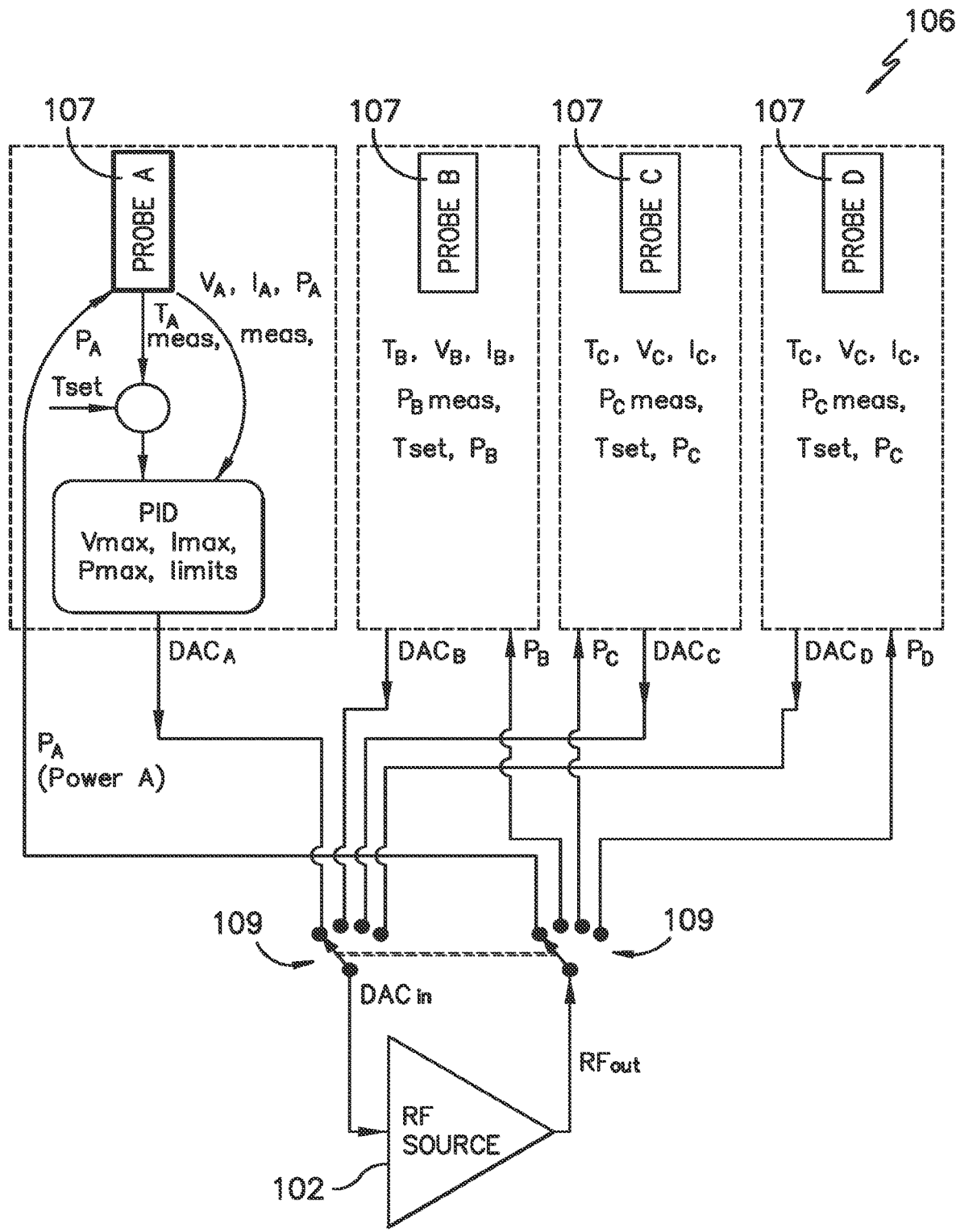
FIG. -6-

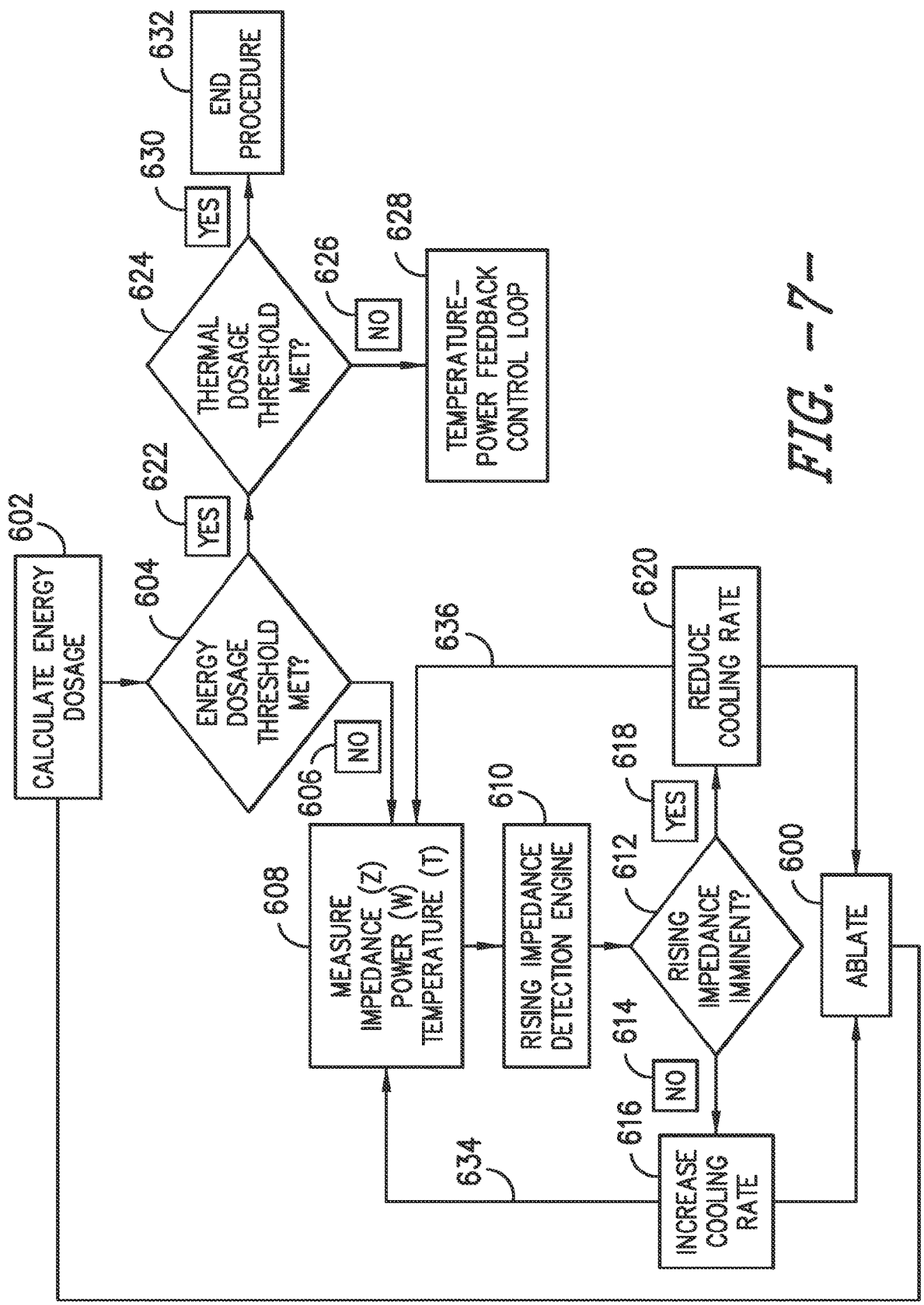
FIG. -7-

SYSTEM AND METHOD FOR ADJUSTING AVAILABLE POWER PER PROBE DURING AN ABLATION PROCEDURE

CROSS-REFERENCE TO RELATED APPLICATIONS

This application is a continuation of U.S. application Ser. No. 16/027,653, filed Jul. 5, 2018. The aforementioned application is incorporated by reference in its entirety for all purposes.

BACKGROUND

Lower back injuries and chronic back pain are a major health problem resulting not only in a debilitating condition for the patient, but also in the consumption of a large proportion of funds allocated for health care, social assistance and disability programs. Disc abnormalities and pain may result from trauma, repetitive use in the workplace, metabolic disorders, inherited proclivity or aging. The existence of adjacent nerve structures and innervation of the disc are very important issues in respect to patient treatment for back pain.

A minimally invasive technique of delivering high-frequency electrical current has been shown to relieve localized pain in many patients. Generally, the high-frequency current used for such procedures is in the radio frequency (RF) range, i.e. between 100 kHz and 1 GHz and more specifically between 300-600 kHz. The RF electrical current is typically delivered from a generator via a plurality of connected electrodes that are placed in a patient's body, in a region of tissue that contains a neural structure suspected of transmitting pain signals to the brain. The electrodes generally include an insulated shaft with an exposed conductive tip to deliver the radio frequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the tissue near an energy delivery device, allowing a higher voltage to be applied without causing an unwanted increase in local tissue temperature. The application of a higher voltage allows regions of tissue further away from the energy delivery device to reach a temperature at which a lesion can form, thus increasing the size/volume of the lesion.

Such procedures can be done using any suitable number of probes, e.g. from one probe up to four probes at a time. In current RF systems, the maximum power of the generator is divided between the connected probes. The amount of power allotted per probe is calculated based on need, therefore, if one probe has higher power needs, it can take power from the other probes. However, this approach can cause complications between probes, resulting in early termination of or incomplete procedures, thereby causing both patient and doctor frustration.

Thus, the present disclosure is directed to systems and methods for adjusting available power per probe during an ablation procedure that addresses the aforementioned issues.

SUMMARY

Objects and advantages of the present disclosure will be set forth in part in the following description, or may be obvious from the description, or may be learned through practice of the present disclosure.

Example aspects of the present disclosure are directed to methods for treating tissue of a patient's body. In one embodiment, the method includes providing an energy source and a controller coupled to a probe assembly. The energy source includes a predetermined power supply. The method also includes detecting, via the controller, a number of probes of the probe assembly connected to the energy source. Each probe has an elongate member with a distal region and a proximal region. The distal region has an electrically-conductive energy delivery device for delivering one of electrical and radiofrequency energy to the patient's body. The method also includes inserting the probes of the probe assembly into the patient's body. Further, the method includes positioning the probes at or near the tissue to be treated of the patient's body. In addition, the method includes allocating, via the energy source, a portion of the predetermined power supply to each of the probes based on the number of probes detected. Thus, the method further includes treating the tissue by controlling the probes based on the allocated power.

In further example aspects of the present disclosure, the step of allocating the portion of the predetermined power supply to each of the probes based on the number of probes detected may include equally dividing the predetermined power supply to each of the probes. In another embodiment, the method may include operating each of the probes in an independent state. For example, in such embodiments, the independent state may correspond to a ready state, an on state, or a complete state.

In further embodiments, the step of treating the tissue by controlling the probes based on the allocated power may include cycling through a treatment procedure for one or more of the probes. In such embodiments, the step of cycling through the treatment procedure for one or more of the probes may include delivering energy from the energy source to each of the probes in succession. For example, in certain embodiments, when cycling through the treatment procedure for one or more of the probes, the method may include omitting cycling through probes that do not have an available power above a certain threshold. For example, in such embodiments, the method may include omitting unconnected probes (e.g. empty connections) and/or probes connected after a certain point. As such, the method may cycle through probes that are in a ready state (but not delivering RF energy).

In additional embodiments, the step of treating the tissue by controlling the probes based on the allocated power may include independently starting or stopping individual treatment procedures for one or more of the probes without affecting the available power to remaining probes. Thus, in certain embodiments, the method may include activating the individual treatment procedures for each of the probes in a sequential order.

In several embodiments, the step of treating the tissue by controlling the probes based on the allocated power may further controlling power supplied to each of the probes as a function of a temperature of that probe.

In yet another embodiment, the energy source may be a generator. In such embodiments, the predetermined power supply of the generator may be at least 80 watts.

In still further embodiments, the method may include limiting power, voltage, or current supplied by the generator to one or more of the probes. For example, in one embodiment, the generator may limit the power supplied to a single probe or probe pair of the probe assembly to 50 watts or less.

Example aspects of the present disclosure are directed to an ablation system for treating tissue in a patient's body. The ablation system includes an energy source, one or more probes connected to the energy source, and a controller communicatively coupled to one or more probes. For example, in one embodiment, the ablation system may include one probe or up to four probes. Each of the probes includes an elongate member having a distal region with an electrically non-conductive outer circumferential portion and a proximal region. The probes further include an electrically conductive energy delivery device extending distally from the electrically non-conductive outer circumferential portion for delivering one of electrical and radiofrequency energy to the patient's body and have an electrically conductive outer circumferential surface. The controller also includes one or more processors and one or more memory devices. The one or more memory devices are configured to store computer-readable instructions that when executed by the one or more processors cause the one or more processors to perform operations. More specifically, the operations include detecting a number of probes connected to the energy source and allocating a portion of the predetermined power supply to each of the probes based on the number of probes detected. It should also be understood that the ablation system may further include any of the additional features as described herein.

Example aspects of the present disclosure are directed to a controller for treating tissue of a patient's body. The controller includes a controller communicatively coupled to one or more probes. The controller includes one or more processors and one or more memory devices. The one or more memory devices are configured to store computer-readable instructions that when executed by the one or more processors cause the one or more processors to perform operations. More specifically, the operations include detecting a number of probes connected to the energy source and allocating a portion of the predetermined power supply to each of the probes based on the number of probes detected. It should also be understood that the controller may further include any of the additional features as described herein.

These and other features, aspects and advantages of the present disclosure will become better understood with reference to the following description and appended claims. The accompanying drawings, which are incorporated in and constitute a part of this specification, illustrate embodiments of the disclosure and, together with the description, explain the principles of the disclosure.

BRIEF DESCRIPTION OF THE DRAWINGS

A full and enabling disclosure of the present disclosure, including the best mode thereof, directed to one of ordinary skill in the art, is set forth in the specification, which refers to the appended figures, in which:

FIG. 1 illustrates a portion of one embodiment of a system for applying radio frequency electrical energy to a patient's body according to the present disclosure;

FIG. 2 illustrates a block diagram of one embodiment of a controller that can be included as part of the ablation system according to the present disclosure;

FIG. 3 illustrates a perspective cut-away view of one embodiment of a distal tip region of a probe assembly according to the present disclosure;

FIG. 4 illustrates two probes placed within an intervertebral disc according to the present disclosure;

FIG. 5 illustrates a flow diagram of one embodiment of a method of treating tissue of a patient's body according to the present disclosure;

FIG. 6 illustrates a schematic diagram of one embodiment of a probe assembly according to the present disclosure; and FIG. 7 illustrates a block diagram of one embodiment of a treatment procedure for actively controlling energy delivered to tissue in the patient's body by controlling an amount of energy delivered by the energy delivery devices and a flow rate of the pumps of the pump assembly according to the present disclosure.

DETAILED DESCRIPTION

Reference will now be made in detail to one or more embodiments of the disclosure, examples of the disclosure, examples of which are illustrated in the drawings. Each example and embodiment is provided by way of explanation of the disclosure, and is not meant as a limitation of the disclosure. For example, features illustrated or described as part of one embodiment may be used with another embodiment to yield still a further embodiment. It is intended that the disclosure include these and other modifications and variations as coming within the scope and spirit of the disclosure.

Before explaining at least one embodiment of the disclosure in detail, it is to be understood that the disclosure is not limited in its application to the details of construction and the arrangement of the components set forth in the following description or illustrated in the drawings. The disclosure is capable of other embodiments or of being practiced or carried out in various ways. Also, it is to be understood that the phraseology and terminology employed herein is for the purpose of description and should not be regarded as limiting.

For the purposes of this disclosure, a lesion refers to any effect achieved through the application of energy to a tissue in a patient's body, and the disclosure is not intended to be limited in this regard. Furthermore, for the purposes of this description, proximal generally indicates that portion of a device or system next to or nearer to a user (when the device is in use), while the term distal generally indicates a portion further away from the user (when the device is in use).

Referring now to the drawings, FIG. 1 illustrates a schematic diagram of one embodiment of an ablation system 100 for treating tissue in a patient's body according to example aspects of the present disclosure. As shown, the ablation system 100 includes a generator 102, a controller 120 communicatively coupled to the generator 102, at least one probe assembly 106 having a plurality of probes 107 coupled to the generator, e.g. via cable 104, and one or more cooling devices 108. More specifically, as shown in the illustrated embodiment, the ablation system 100 includes four probes 107. It should be understood that the ablation system 100 may include any suitable number of probes 107, including one probe up to four probes and more.

In addition, as shown in the illustrated embodiment, the generator 102 may be a radio frequency (RF) generator, but may optionally be any energy source that may deliver other forms of energy, including but not limited to microwave energy, thermal energy, ultrasound and optical energy. In one embodiment, the generator 102 is operable to communicate with one more devices, for example with the probes 107 and the one or more cooling devices 108. Such communication may be unidirectional or bidirectional depending on the devices used and the procedure performed. In addition, as shown, the cooling devices 108 may be coupled to the generator 102 via a pump cable 110. Further, as shown, the ablation system 10 may also include one or more proximal cooling supply tubes 112 and one or more proximal cooling return tubes 114.

In addition, as shown, a distal region 124 of the cable 104 may include a splitter 130 that divides the cable 104 into two distal ends 136 such that the probes 107 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two distal ends 136 of the cable 104 terminate in connectors 140 operable to couple to the probes 107 and establish an electrical connection between the probes 107 and the generator 102. In alternate embodiments, the system 100 may include a separate cable for each probe assembly 106 being used to couple the probes 107 to the generator 102. Alternatively, the splitter 130 may include more than two distal ends. Such a connector is useful in embodiments having more than two devices connected to the generator 102, for example, if more than two probe assemblies are being used.

The cooling device(s) 108 may include any means of reducing a temperature of material located at and proximate to one or more of the probes 107. For example, the cooling devices 108 may include one or more peristaltic pumps operable to circulate a fluid from the cooling devices 108 through one or more proximal cooling supply tubes 112, the probes 107, one or more proximal cooling return tubes 114 and back to the one or more cooling devices 108. The fluid may be water or any other suitable fluid.

Referring to FIGS. 1 and 2, the controller 120 is configured for facilitating communication between the various components of the system 100. For example, in one embodiment, the controller 120 facilitates communication between the cooling devices 108 and the generator 102. In this way, feedback control is established between the cooling device(s) 108 and the generator 102. The feedback control may include the generator 102, the probes 107, and the cooling devices 108, although any feedback between any devices is within the scope of the present disclosure. The feedback control may be implemented, for example, in a control module which may be a component of the generator 102 or separate from the generator 102. In such embodiments, the generator 102 is operable to communicate bi-directionally with the probes 107 as well as with the cooling devices 108. In the context of this disclosure, bi-directional communication refers to the capability of a device to both receive a signal from and send a signal to another device.

Further, as shown particularly in FIG. 2, the controller 120 may include one or more processor(s) 200 and associated memory device(s) 202 configured to perform a variety of computer-implemented functions (e.g., performing the methods, steps, calculations and the like and storing relevant data as disclosed herein). Moreover, the memory device(s) 202 may be configured to store computer-readable instructions that when executed by the one or more processors 200 cause the one or more processors 200 to perform operations. For example, in one embodiment, the operations may include detecting a number of probes 107 connected to the generator 102 and allocating a portion of its power supply to each of the probes 107 based on the number of probes detected.

Additionally, the controller 120 may also include a communications module 204 to facilitate communications between the controller 120 and the various components of the system 100, e.g. any of the components of FIG. 1. Further, the communications module 204 may include a sensor interface 206 (e.g., one or more analog-to-digital converters) to permit signals transmitted from one or more sensors 208, 210 to be converted into signals that can be understood and processed by the processors 200. It should be appreciated that the sensors 208, 210 may be communicatively coupled to the sensor interface 206 using any suitable means. For example, as shown, the sensors 208, 210 may be coupled to the sensor interface 206 via a wired connection. However, in other embodiments, the sensors 208, 210 may be coupled to the sensor interface 206 via a wireless connection, such as by using any suitable wireless communications protocol known in the art. As such, the processor 200 may be configured to receive one or more signals from the sensors 208,210.

As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. The processor 200 is also configured to compute advanced control algorithms and communicate to a variety of Ethernet or serial-based protocols (Modbus, OPC, CAN, etc.). Additionally, the memory device(s) 202 may generally include memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 202 may generally be configured to store suitable computer-readable instructions that, when implemented by the processor(s) 200, configure the controller 120 to perform the various functions as described herein.

As an example, the controller 120 may receive temperature measurements from one or more of the plurality of probes 107. Based on the temperature measurements, the controller 120 may perform some action, such as modulating the power that is sent to the probes 107. Thus, the probes 107 may be individually controlled based on their respective temperature measurements. For example, power to each of the probes 107 can be increased when a temperature measurement is low or decreased when a measurement is high. This variation of power may be different for each probe assembly. In some cases, the controller 120 may terminate power to one or more probes 107. Thus, the controller 120 may receive a signal (e.g. temperature measurement) from one or more of probes 107, determine the appropriate action, and send a signal (e.g. decreased or increased power) back to one or more of the probes 107. Alternatively, the controller 120 may send a signal to the cooling devices 108 to either increase or decrease the flow rate or degree of cooling being supplied to one or more of the probes 107.

In several embodiments, the cooling devices 108 may reduce the rate of cooling or disengage depending on the distance between the probes 107. For example, when the distance is small enough such that a sufficient current density exists in the region to achieve a desired temperature, little or no cooling may be required. In such an embodiment, energy is preferentially concentrated between the energy delivery devices 192 through a region of tissue to be treated, thereby creating a strip lesion. A strip lesion is characterized by an oblong volume of heated tissue that is formed when an active electrode is near a return electrode of similar dimensions. This occurs because at a given power, the current density is preferentially concentrated between the electrodes and a rise in temperature results from current density.

The cooling devices 108 may also communicate with the generator 102 and/or the controller 120 to alert the generator 102 to one or more possible errors and/or anomalies associated with the cooling devices 108. For example, if cooling flow is impeded or if a lid of one or more of the cooling devices 108 is opened. The controller 120 may then act on the error signal by at least one of alerting a user, aborting the procedure and modifying an action.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors although other connector types are intended to be within the scope of the present disclosure.

In addition, as shown in FIG. 1, each of the probes 107 may include a proximal region 160, a handle 180, a hollow elongate shaft 184, and a distal tip region 190 that includes the one or more energy delivery devices 192. Further, as shown, the proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probes 107, but alternate embodiments with rigid tubes are possible.

Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe cable connector 172 may be located at a proximal end of the probe assembly cable 170 and may be operable to reversibly couple to one of the connectors 140, thus establishing an electrical connection between the generator 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the generator 102 to the one or more energy delivery devices 192 as well as to connect multiple temperature sensing devices to the generator 102 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the disclosure is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc, however, different sizes of active regions, all of which are within the scope of the present disclosure, may be used depending on the specific procedure being performed. In some embodiments, feedback from the generator 102 may automatically adjust the exposed area of the energy delivery device 192 in response to a given measurement such as impedance or temperature. For example, in one embodiment, the energy delivery devices 192 may maximize energy delivered to the tissue by implementing at least one additional feedback control, such as a rising impedance value.

Referring now to FIG. 3, a perspective cut-away view of one embodiment of the distal tip region 190 of the probe assembly 106 is illustrated. As shown, the distal tip region 190 includes one or more temperature sensing elements 402 which are operable to measure the temperature at and proximate to the one or more energy delivery devices 192. The temperature sensing elements 402 may include one or more thermocouples, thermometers, thermistors, optical fluorescent sensors or any other means of sensing temperature. In one embodiment, the temperature sensing elements 402 are connected to the generator 102 via probe assembly cable 170 and cable 104 although any means of communication between the temperature sensing elements 402 and the generator 102, including wireless protocols, are included within the scope of the present disclosure. More specifically, as shown, the temperature sensing element(s) 402 may include a thermocouple junction made by joining a stainless steel hypotube 406 to a constantan wire 410, wherein the constantan wire 410 is insulated by insulation 412. In this embodiment, the junction of hypotube 406 and the constantan wire 410 is made by laser welding, although any other means of joining two metals may be used. Furthermore, in this embodiment, the hypotube 406 and the constantan wire 410 extend through a lumen of the elongate shaft 184 and connect to the probe assembly cable 170 within the handle 180.

Further, as shown, the temperature sensing element 402 of each probe 107 protrudes beyond the energy delivery device 192. Placing the temperature sensing elements 402 at this location, rather than within a lumen 450 defined by the energy delivery device 192, is beneficial because it allows the temperature sensing element 402 to provide a more accurate indication of the temperature of tissue proximate to the energy delivery device 192. This is due to the fact that, when extended beyond the energy delivery device 192, the temperature sensing element 402 will not be as affected by the cooling fluid flowing within the lumen 450 as it would be were it located within lumen 450. Thus, in such embodiments, the probe assembly 106 includes a protrusion protruding from the distal region of the probe assembly, whereby the protrusion is a component of the temperature sensing element 402.

Referring still to FIG. 3, the probes 107 may further include one or more secondary temperature sensing elements 404 located within the elongate shaft 184 at some distance away from the energy delivery device 192, and positioned adjacent a wall of the elongate shaft 184. The secondary temperature sensing elements 404 may similarly include one or more thermocouples, thermometers, thermistors, optical fluorescent sensors or any other means of sensing temperature. For example, as shown, the secondary temperature sensing element 404 is a thermocouple made by joining copper and constantan thermocouple wires, designated as 420 and 422 respectively. Further, in certain embodiments, the copper and constantan wires 420 and 422 may extend through a lumen of the elongate shaft 184 and may connect to the probe assembly cable 170 within the handle 180.

In addition, the probes 107 may further include a thermal insulator 430 located proximate to any of the temperature sensing elements 402, 404. As such, the thermal insulator 430 may be made from any thermally insulating material, for example silicone and may be used to insulate any temperature sensing element from other components of the probe assembly 106, so that the temperature sensing element will be able to more accurately measure the temperature of the surrounding tissue. More specifically, as shown, the thermal insulator 430 is used to insulate the temperature sensing element 404 from cooling fluid passing through the shaft supply tube 302 and the shaft return tube 304.

In further embodiments, the probes 107 may also include a radiopaque marker 440 incorporated somewhere along the elongate shaft 184. For example, as shown in FIG. 3, an optimal location for a radiopaque marker may be at or proximate to the distal tip region 190, adjacent the energy delivery device 192. The radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum and other high-density metals as well as radiopaque polymeric compounds. Various methods for incorporating radiopaque markers into or onto medical devices may be used, and the present disclosure is not limited in this regard.

Referring now to FIG. 4, the ablation system 100 of the present disclosure may further include one or more introducer tubes 802. Generally, introducer tubes may include a proximal end, a distal end, and a longitudinal bore extending therebetween. Thus, the introducer tubes 802 (when used) are operable to easily and securely couple with the probes 107. For example, the proximal end of the introducer tubes 802 may be fitted with a connector able to mate reversibly with handle 180 of one of the probes 107. An introducer tube 802 may be used to gain access to a treatment site within a patient's body and a hollow elongate shaft 184 of a probe 107 may be introduced to the treatment site through the longitudinal bore of the introducer tube 802. The introducer tubes 802 may be made of various materials, as is known in the art and, if the material is electrically conductive, the introducer tubes may be electrically insulated along all or part of their length, to prevent energy from being conducted to undesirable locations within a patient's body. In some embodiments, the elongate shaft 184 may be electrically conductive, and an introducer tube 802 may function to insulate the shaft 184 leaving the energy delivery device 192 exposed for treatment.

In additional embodiments, the ablation system 100 may also include one or more stylets. A stylet may have a beveled tip to facilitate insertion of the one or more introducer tubes into a patient's body. Various forms of stylets are well known in the art and the present disclosure is not limited to include only one specific form. Further, as described above with respect to the introducer tubes, the stylets may be operable to connect to a power source and may therefore form part of an electrical current impedance monitor. In other embodiments, one or more of the probes 107 may form part of an electrical current impedance monitor. Thus, the controller 120 may receive impedance measurements from one or more of the stylets, the introducer tubes, and/or the probes 107 and may perform an action, such as alerting a user to an incorrect placement of an energy delivery device 192, based on the impedance measurements.

In one embodiment, the plurality of probes 107 may be operated in a bipolar mode. For example, FIG. 4 illustrates one embodiment of two probes 107, wherein the distal tip regions 190 thereof are located within an intervertebral disc 800. In such embodiments, electrical energy is delivered to the probes 107 and this energy is preferentially concentrated therebetween through a region of tissue to be treated (i.e. an area of the intervertebral disc 800). The region of tissue to be treated is thus heated by the energy concentrated between the probes 107. In other embodiments, the probes 107 may be operated in a monopolar mode, in which case an additional grounding pad is required on the surface of a body of a patient, as is known in the art. Any combination of bipolar, monopolar, or other suitable treatment procedures may also be used. Further, as mentioned, it should be understood that the system 100 may include more than two probes 107. For example, in some embodiments, three probes 107 may be used and the probes 107 may be operated in a triphasic mode, whereby the phase of the current being supplied differs for each probe 107.

Referring now to FIG. 5, a flow diagram of one embodiment of a method 500 for treating tissue of a patient's body, such as an intervertebral disc 800, using the ablation system 100 described herein is illustrated. As shown at 502, the method 500 may include providing an energy source and a controller coupled to a probe assembly 106. Further, the energy source, e.g. the generator 102, has a predetermined power supply. For example, in one embodiment, the predetermined power supply may be up to 80 watts (W).

As shown at 504, the method 500 includes detecting, via the controller 120, a number of probes 107 of the probe assembly 106 connected to the energy source. As shown 506, the method 500 includes inserting the plurality of probes 107 into the patient's body. As shown at 508, the method 500 includes positioning the plurality of probes 107 at or near the tissue of the patient's body to be treated. For example, in one embodiment, with a patient lying on a radiolucent table, fluoroscopic guidance may be used to percutaneously insert an introducer with a stylet to access the posterior of an intervertebral disc 800. In addition to fluoroscopy, other aids, including but not limited to impedance monitoring and tactile feedback, may be used to assist a user to position the introducer and/or probes 107 within the patient's body.

Referring still to FIG. 5, as shown at 510, the method 500 may also include allocating, via the energy source 102, a portion of the predetermined power supply to each of the probes 107 based on the number of probes detected of probes 107. More specifically, in one embodiment, the predetermined power supply may be equally divided amongst each of the probes 107. As such, the independent control and higher power levels allow each probe 107 to receive an equal amount of power per channel. For example, when two or more probes are connected to the generator 102, the power may be evenly divided amongst the probes 107 at the beginning of a treatment procedure. Therefore, for a two-probe procedure utilizing an 80-watt generator, each probe 107 may have has access to 40 W. Similarly, for three- and four-probe procedures, each probe 107 may have access to 27 W and 20 W, respectively.

As shown at 512, the method 500 further includes treating the tissue by controlling the probes 107 based on the allocated power. For example, in one embodiment, the method 500 may include operating each of the probes 107 in an independent state. Thus, individual treatment procedures for each of the probes 107 may be independently started or stopped without affecting the available power to remaining probes 107, thereby avoiding entanglement of temperature feedback control on each probe 107. In further embodiments, the ablation system 100 may cycle through a treatment procedure for one or more of the probes 107. More specifically, in certain embodiments, the method 500 may include activating the individual treatment procedures for each of the probes in a sequential order. In addition, the ablation system 100 may omit cycling through treatment procedures of probes 107 that do not have an available power above a certain threshold, thereby maximizing energy availability. This setup eliminates dependencies due to power sharing across active probes. In several embodiments, the ablation system 100 may control power supplied to each of the probes 107 as a function of a temperature of that probe.

Referring now to FIG. 6, a probe assembly 106 having four probes 107, namely Probe A, Probe B, Probe C, and Probe D, is illustrated to further illustrated example aspects of the present disclosure. The independent states described herein may correspond to a "ready" state, an "on" state, or a "complete" state. Probe A is in the "on" state, whereas Probes B, C, and D are in the "ready" state. Further, as shown, each probe has access to the RF source 102 during its respective time slot via, e.g. switches 109. Thus, in certain embodiments, the system 100 may limit power, voltage, or current supplied by the generator 102 to one or more of the probes 107. For example, in one embodiment, the generator 102 may limit the power supplied to a single probe or probe pair of the probe assembly to 50 watts or less. In such embodiments, the system 100 can be operated in a bipolar mode (where probes act in pairs instead of individually). As such, a single pair of probes may be limited to 50 W (similar to a single probe situation), whereas two probe pairs may be limited to 40 W each (similar to a two-probe situation).

During the "ready" state, a connected probe 107 is not active (i.e. the probe 107 is not delivering energy). As used herein, a connected probe generally refers to a probe for which a valid thermocouple detected. As such, the "ready" state is characterized by low-power impedance measurements on all connected probes 107. In addition, one or more bursts of low-voltage output may be provided to the connected probes such that the RF voltage and current can be measured. Thus, the probe impedance and temperature can also be computed during the "ready" state as a function of the measured RF voltage and current. During the "on" state, the connected probe 107 is active (i.e. the probe 107 is delivering energy). As used herein, an active probe generally refers to a probe to which RF output is delivered. For a single active probe operating in the "on" state, RF output is delivered continuously under temperature feedback control as described herein and is subject to RF output limits. For multiple probes, RF output is delivered for a certain time period corresponding to each active probe 107. In such embodiments, the amplitude of the RF during each time period can be controlled by the temperature feedback loop corresponding to that probe 107 and is subject to RF output limits. In addition, low-power impedance measurements can continue to be made on all non-active, connected probes 107, with one or more bursts of low-voltage output being provided at the beginning of the time period corresponding to the non-active, connected probe(s) 107. Thus, the RF voltage and current can be measured and the probe impedance can be computed therefrom. In addition, during the "on" state, the RF power can be measured for each connected probe 107. During the "complete" state, the connected probe(s) 107 is non-active (i.e. RF energy delivery is turned off). As used hereon, a non-active probe generally refers to a connected probe to which no RF output is delivered. In addition, the final measured values are maintained and the system 100 proceeds to the "ready" state after a certain time period or when the active area corresponding to the probe 107 is pressed.

During the individual treatment procedures, a treatment protocol such as the cooling supplied to the respective probe 107 and/or the power transmitted to the probe 107 may be adjusted and/or controlled to maintain a desirable treatment area shape, size and uniformity. More specifically, the method 500 may include actively controlling energy delivered to the tissue by controlling both an amount of energy delivered through the energy delivery devices 192 and individually controlling the flow rate of the cooling devices 108. In further embodiments, the generator 102 may control the energy delivered to the tissue based on the measured temperature measured by the temperature sensing element (s) 402 and/or impedance sensors.

More specifically, as shown in FIG. 7, a block diagram of one embodiment of a treatment procedure for treating a patient's tissues is illustrated. As shown at 600, ablation is initialized. As shown at 602, the energy dosage may be calculated using simple numerical integration techniques. As shown at 604, the calculated energy dosage may then be compared against a preset energy dosage threshold. If the dosage is not satisfied as shown at 606, the procedure continues to 608 to mitigate rising impedance of the internally-cooled probes 107 during the treatment procedure. More specifically, as shown, one or more procedure parameters are monitored while delivering the energy from the generator 102 to the tissue through the energy delivery devices 192. The procedure parameter(s) described herein may include, for example, a temperature of the tissue, an impedance of the tissue, a power demand of the energy delivery device 192, or similar, or combinations thereof. Further, as shown, the procedure parameter(s) 608 may be fed into a rising impedance detection engine 610. As shown at 612, the rising impedance detection engine 610 is configured to determine, e.g. in real-time, whether a rising impedance event is imminent based on the received procedure parameter(s) 608. The rising impedance detection engine 610 can then determine a command for the cooling devices 108 based on whether the rising impedance event is likely to occur in the predetermined time period.

If not imminent, as shown at 614, the cooling rate can be increased, e.g. by increasing pump speed of the cooling devices 108 as shown at 616. After the cooling rate is increased, the ablation 600 continues. If a rising impedance event is imminent, as shown at 618, the cooling rate can be reduced, e.g. by decreasing the pump speed of the cooling devices 108 as shown at 620. Further, as shown, the system operates using closed-loop feedback control 634, 636.

Once the energy dosage threshold is satisfied, as shown at 622, the treatment procedure is configured to check if the thermal dosage threshold has been satisfied as shown at 624.

If the thermal dosage has not been satisfied, as shown at 626, the treatment procedure proceeds through the independent temperature-power feedback control loop as shown at 628. More specifically, in certain embodiments, the amount of energy delivered through the energy delivery device 192 may be controlled by defining a predetermined threshold temperature for treating the tissue, ramping up the temperature of the tissue via the generator 102 through the energy delivery device 192 to the predetermined threshold temperature, and maintaining the temperature of the tissue at the predetermined threshold temperature to create a lesion in the tissue. In such embodiments, the temperature of the tissue may be maintained at the predetermined threshold temperature as a function of at least one of a power ramp rate, an impedance level, an impedance ramp rate, and/or a ratio of impedance to power.

Only when the thermal dosage threshold has been satisfied, as shown at 630, the procedure terminates as shown at 632. Following treatment, energy delivery and cooling may be stopped and the probes 107 are removed from the introducers, where used. A fluid such as an antibiotic or contrast agent may be injected through the introducers, followed by removal of the introducers. Alternatively, the distal tips of the probes 107 may be sharp and sufficiently strong to pierce tissue so that introducers may not be required. As mentioned above, positioning the probes 107, and more specifically the energy delivery devices 192, within the patient's body, may be assisted by various means, including but not limited to fluoroscopic imaging, impedance monitoring and tactile feedback. Additionally, some embodiments of this method may include one or more steps of inserting or removing material into a patient's body.

A system of the present disclosure may be used in various medical procedures where usage of an energy delivery device may prove beneficial. Specifically, the system of the present disclosure is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probes 107 with an appropriate feedback control system as described herein also contributes to the uniformity of the treatment. The cooling distal tip regions 190 of the probes 107 helps to prevent excessively high temperatures in these regions which may lead to tissue adhering to the probes 107 as well as an increase in the impedance of tissue surrounding the distal tip regions 190 of the probes 107. Thus, by cooling the distal tip regions 190 of the probes 107, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

It should be noted that the term radiopaque marker as used herein denotes any addition or reduction of material that increases or reduces the radiopacity of the device. Furthermore, the terms probe assembly, introducer, stylet etc. are not intended to be limiting and denote any medical and surgical tools that can be used to perform similar functions to those described. In addition, the disclosure is not limited to be used in the clinical applications disclosed herein, and other medical and surgical procedures wherein a device of the present disclosure would be useful are included within the scope of the present disclosure.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

The invention claimed is:

1. A method of treating tissue of a patient's body, the method comprising:
   providing an energy source and a controller coupled to a probe assembly, the energy source comprising a predetermined power supply;
   detecting, via the controller, a number of probes of the probe assembly connected to the energy source, each probe having an electrically-conductive energy delivery device for delivering one of electrical and radiofrequency (RF) energy to the patient's body;
   positioning the probes at or near the tissue to be treated of the patient's body;
   dividing, via the energy source, the predetermined power supply among each of the probes based on the number of probes detected; and
   treating the tissue by independently controlling each of the probes using the divided power, wherein each of the probes is controlled in a ready state where a thermocouple measurement of a connected probe is detectable and the connected probe is not delivering power,
   wherein individual treatment procedures for each of the probes are independently started or stopped without affecting available power to remaining probes.

2. The method of claim 1, wherein in the ready state, providing one or more bursts of low-voltage output to at least one of the probes such and measuring at least one of a corresponding RF voltage and current.

3. The method of claim 2, further comprising determining at least one of an impedance and a temperature of the corresponding probe as a function of a measured RF voltage and current.

4. The method of claim 1, wherein treating the tissue by independently controlling each of the probes using the divided power further comprises controlling power supplied to each of the probes as a function of a temperature of that probe.

5. The method of claim 1, wherein the probes include a first probe and a second probe,
wherein treating the tissue by independently controlling each of the probes based on the divided power further comprises controlling the first and second probes in an on state, where in the on state the thermocouple measurement of the connected probe is detectable and the connected probe is delivering power, and the RF energy is delivered from each of the first and second probes for a corresponding first and second time period,
wherein, in the on state, an amplitude of the RF energy delivered the first and second probe is controlled by a corresponding temperature of the first and second probe.

6. The method of claim 1, wherein treating the tissue by independently controlling each of the probes based on the divided power further comprises cycling through a treatment procedure for one or more of the probes, wherein cycling through the treatment procedure for one or more of the probes further comprises delivering energy from the energy source to each of the probes in succession.

7. The method of claim 6, wherein, when cycling through the treatment procedure for one or more of the probes, the method omits cycling through probes that do not have an available power above a certain threshold.

8. The method of claim 1, further comprising activating the individual treatment procedures for each of the probes in at least one of a sequential order or simultaneously.

9. The method of claim 1, wherein treating tissue by independently controlling each of the probes further comprises limiting the power provided to a pair of the probes to a threshold power amount such that the pair of probes operate in a bipolar mode.

10. An ablation system for treating tissue in a patient's body, the ablation system comprising:
an energy source comprising a predetermined power supply;
one or more probes connected to the energy source, each comprising an electrically conductive energy delivery device for delivering one of electrical and radiofrequency (RF) energy to the patient's body;
a controller communicatively coupled to one or more probes, the controller including a processor and a memory device, the memory device configured to store computer-readable instructions that when executed by the processor cause the processor to perform operations, the operations comprising:
detecting a number of probes connected to the energy source; and
dividing the predetermined power supply among each of the probes based on the number of probes detected; and
treating the tissue by independently controlling each of the probes using the divided power, wherein each of the probes is controlled in a ready state where a thermocouple measurement of a connected probe is detectable and the connected probe is not delivering power,
wherein individual treatment procedures for each of the probes are independently started or stopped without affecting available power to remaining probes.

11. The ablation system of claim 10, wherein in the ready state, one or more bursts of low-voltage output is provided to at least one of the probes such that at least one of a corresponding RF voltage and current can be measured.

12. The ablation system of claim 11, wherein the controller operations further include:
determining at least one of an impedance and a temperature of the corresponding probe as a function of a measured RF voltage and current.

13. The ablation system of claim 10, wherein treating the tissue by independently controlling each of the probes based on the divided power further comprises controlling power supplied to each of the probes as a function of a temperature of that probe.

14. The ablation system of claim 10, wherein the probes include a first probe and a second probe,
wherein the first and second probes are controlled in an on state, where in the on state the thermocouple measurement of the connected probe is detectable and the connected probe is delivering power, and the RF energy is delivered from each of the first and second probes for a corresponding first and second time period,
wherein, in the on state, an amplitude of the RF energy delivered the first and second probe is controlled by a corresponding temperature of the first and second probe.

15. The ablation system of claim 10, wherein treating the tissue by independently controlling each of the probes based on the divided power further comprises cycling through a treatment procedure for each of the probes, wherein cycling through the treatment procedure for one or more of the probes further comprises delivering energy from the energy source to each of the probes in succession.

16. The ablation system of claim 15, further comprising omitting treatment procedures for probes that do not have an available power above a certain threshold.

17. The ablation system of claim 10, further comprising limiting the power provided to a pair of the probes to a threshold power amount such that the pair of probes operate in a bipolar mode.

18. The ablation system of claim 10, wherein the electrically conductive energy delivery device of each at least one of the one or more probes extends distally from an electrically non-conductive outer circumferential portion.

19. The ablation system of claim 10, wherein the number of probes comprises from one probe to four probes and the energy source comprises a generator, the predetermined power supply of the generator comprising at least 80 watts.

* * * * *